United States Patent [19]

Murao et al.

[11] Patent Number: 4,769,323

[45] Date of Patent: Sep. 6, 1988

[54] METHOD FOR FRACTIONAL DETERMINATION OF ASPARTATE AMINOTRANSFERASE ISOZYMES, AND COMPOSITION THEREFOR

[76] Inventors: Sawao Murao, 8-12, Horiagemidori-machi 2-cho, Sakai-shi, Osaka; Toyokazu Nishino, 15-1, Ueno-cho, Ibaragi-shi, Osaka, both of Japan

[21] Appl. No.: 688,423

[22] Filed: Jan. 2, 1985

[30] Foreign Application Priority Data

Jan. 12, 1984 [JP] Japan .................................. 59-4495

[51] Int. Cl.⁴ ...................... C12Q 1/52; C12N 9/99; C12N 9/10; C12R 1/465
[52] U.S. Cl. .................................. 435/16; 435/184; 435/193; 435/810; 435/886
[58] Field of Search .................. 435/15, 16, 24, 23, 435/184, 193, 219, 220, 222, 810, 886

[56] References Cited

U.S. PATENT DOCUMENTS 4,477,566  10/1984  Ricci et al. ......................... 435/184

OTHER PUBLICATIONS

Murao et al., Agric. Biol. Chem., 48(8):2163–2166 (Aug. 1984).
Metzler et al., Fed. Proc., 41(8):2432–2436 (1982).
Ottesen et al. and Narahashi, Methods in Enzymology, vol. 19, "Proteolytic Enzymes", Academic Press, New York, 199–215 and 651–664 (1970).
Shimizu et al., Agric. Biol. Chem., 47(8):1775–1782 (1983).
Sandmeier et al., J. Biol. Chem., 255(21):10284–10289 (1980).

Primary Examiner—Esther M. Kepplinger
Attorney, Agent, or Firm—Wegner & Bretschneider

[57] ABSTRACT

A method of inactivating cytosolic aspartate aminotransferase isozyme comprises addition of a specific inhibitory enzyme.

A method for the fractional determination of aspartate aminotransferase isozyme activities, which comprises (a) inactivating the cytosolic aspartate aminotransferase isozyme in a reaction mixture containing the specimen by the addition of a specific inhibitory enzyme, followed by determination of the residual mitochondrial aspartate aminotransferase isozyme activity, and (b) determination of the cytosolic isozyme activity by subtracting the activity of mitochondrial isozyme determined in (a) from the total activity of aspartate aminotransferase isozymes.

A cytosolic aspartate aminotransferase isozyme inhibiting composition contains an effective cytosolic aspartate aminotransferase isozyme inhibitory amount of a specific inhibitory enzyme.

12 Claims, 1 Drawing Sheet

METHOD FOR FRACTIONAL DETERMINATION OF ASPARTATE AMINOTRANSFERASE ISOZYMES, AND COMPOSITION THEREFOR

BACKGROUND OF THE INVENTION

1. Field of the Invention

The present invention relates to a method of inactivating cytosolic aspartate aminotransferase isozyme comprising addition of a specific inhibitory enzyme, to a method for the fractional determinations of aspartate aminotransferase (EC 2.6.1.1, systematic name=L-Aspartate: 2-oxoglutarate aminotransferase; another name=Glutamic-oxaloacetic transaminase; hereinafter referred to as AST) isozymes present in specimens of blood serum, blood plasma, etc., and to a composition therefor. More particularly, the invention relates to a method for the practional determination of two AST isozymes, which comprises (a) inactivating the cytosolic AST isozyme thereof with an enzyme which specifically inactivates this isozyme, followed by determining the residual isozyme activity, i.e. the mitochondrial AST isozyme according to a known method for AST activity determination; and (b) calculating the activity of the cytosolic AST by subtracting the activity of mitochondrial AST determined in the above-mentioned (a) from the total activity of AST isozymes which has been estimated according to a known method.

2. Description of the Prior Art

AST isozymes are known as enzymes occurring in the liver, myocardium, brain, skeletal muscle, kidney and the like, and catalyzing the following reaction:

L-Aspartate+2−Oxoglutarate
⇌Oxaloacetate+L−Glutamate

The AST isozymes include two kinds of isozymes different in localization, one being cytosolic AST (hereinafter referred to as "s-AST") and the other being mitochondrial AST (hereinafter referred to as "m-AST"). The fractional determination thereof is useful for the clinical diagnosis of hepatitis, myocardial infarction, etc.

Up to now the assay of AST isozymes has been performed according to a chromatographic method using an anionic ion exchanger (Rinsho Kagaku, 5, 163, (1977)), an imnunochemical method, or an electrophoretic method. However, these methods have various disadvantages such that the procedure is complicated and time-consuming and the sensitivity and accuracy of estimation are insufficient.

On the susceptibility of AST isozymes to proteases, there are reports by E. Sandmeier et al. (J. Biol. Chem., 255, 10284–10289 (1980)) and by D E. Metzler et al. (Federation Proceedings, 41, 2432–2436 (1982)). E. Sandmeier et al. have reported that trypsin limitedly cleaved m-AST to inactive it, and in a preliminary experiment, a similar proteolytic cleavage of s-AST was observed. D. E. Metzler et al. have described that m-AST was inactivated by trypsin though more slowly than s-AST.

SUMMARY OF THE INVENTION

For the purpose of achieving the fractional determinations of AST isozymes, the present inventors searched for substances inhibiting the activity of one of these isozymes. It has been revealed that a strain of genus Streptomyces which was found in soil microorganisms by the present inventors produces a substance which inhibits s-AST but not m-AST at all. Moreover, from the purification and isolation and the examination of physical and chemical properties, this substance has proved unexpectedly to be a proteolytic enzyme and more specifically to belong to the serine protease group.

Accordingly, the present inventors are the first to discover an enzyme acting as a specific inhibitor of s-AST.

Further, known proteases other than the above enzyme found by the present inventors were examined for AST-inhibiting activity. Thus, the present inventors have found that certain enzymes belonging to the serine protease group exhibit AST-inhibiting activity similar to that of the above-mentioned protease. Based on the above finding, the present invention has been accomplished. According to the method of the present invention, each AST isozyme can be determined simply and accurately without prior separation of the isozymes.

According to the present invention, there is provided a method of inactivating cytosolic aspartate aminotransferase isozyme comprising addition of a specific inhibitory enzyme.

According to another aspect of the present invention, there is provided a method for the fractional determination of aspartate aminotransferase isozyme activities, which comprises (a) inactivating the cytosolic aspartate aminotransferase isozyme in a reaction mixture containing the specimen by the addition of a specific inhibitory enzyme, followed by determination of the residual mitochondrial aspartate aminotransferase isozyme activity, and (b) determination of the cytosolic isozyme activity by subtracting the activity of mitochondrial isozyme determined in (a) from the total activity of AST isozymes.

According to still another aspect of the present invention, there is provided a cytosolic aspartate aminotransferase isozyme inhibiting composition containing an effective cytosolic aspartate aminotransferase isozyme inhibitory amount of a specific inhibitory enzyme.

Figure 1:
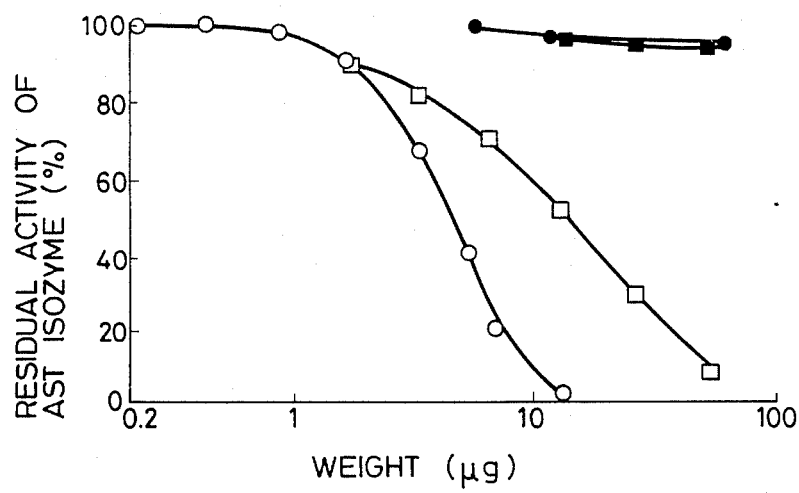
FIG. 1 shows the relationship between doses (weights) of s-AST-inactivating enzymes and AST inhibitory activities thereof when the enzyme produced by *Streptomyces violaceochromogenes* No. 9722 and subtilisin BPN' are used as AST-inactivating enzymes.

— ○ —: s-AST inhibitory activity of the enzyme produced
by *Streptomyces violaceochromogenes* No. 9722;
—●—: m-AST inhibitory activity of the same;
—□—: s-AST inhibitory activity of subtilisin BPN'; and
—■—: m-AST inhibitory activity of the same

DETAILED DESCRIPTION OF PREFERRED EMBODIMENTS

In the present invention, any enzyme may be used that inhibits s-AST specifically but not m-AST at all. Such enzymes include, for example; the protease produced by the strain No. 9722 of genus Streptomyces that the present inventors found by screening strains isolated from soil; Pronase (an alkaline protease produced by a strain of *Streptomyces griseus*; and subtilisin (an alkaline protease produced by a strain of genus Bacillus). All of these enzymes belong to the serine protease. Of these enzymes, specially preferred is the protease produced by the strain No. 9722 of genus Streptomyces.

The strain No. 9722 has the following mycological properties:

(a) Morphology

Aerial hyphae of about 1 $\mu$ in diameter extend from substrate hyphae and have open spiral chains of spores on the top. The aerial hyphae have simple branching and no verticillus. The spore is in elliptical or cylindrical form and with smooth surface. The number of spores in chains is at least 10. The size of spore is 0.6–1.2 $\mu \times 0.7$–1.8 $\mu$. No hairy spore, sclerotium, and sporangium are observed.

(b) Growth in various medium

Table 1 shows growth of the strain after cultivation in various media for 14–21 days.

TABLE 1

| Medium | Growth | Color of substrate mycelium (reverse color) | Aerial mycelium (amount, color) | Soluble pigment |
|---|---|---|---|---|
| Sucrose-Nitrate agar | Good | Yellowish white | Rich, brown-gray | Deep red-purple |
| Glucose-Asparagine agar | Fair | Yellowish white | Ordinary, brown-gray | Light red-purple |
| Glycerol-Asparagine agar | Fair | Yellowish white | Ordinary, brown-gray | Red-purple |
| Inorganic Salts-Starch agar | Good | Cream color | Rich, grayish olive | None |
| Tyrosine agar | Good | Dull red-purple | Rich grayish olive | Deep red-purple |
| Nutrient agar | Good | Cream color | Rich, brown-gray | Yellowish Brown |
| Yeast extract-Malt extract agar | Fair | Cream color | Poor, light brown-gray | Yellowish Brown |
| Oatmeal agar | Fair | Yellowish white | Poor, light brown-gray | None |
| Peptone-Yeast extract-Iron agar | Fair | Yellowish white | Ordinary, light brown-gray | Yellowish Brown |

(c) Physiological properties (i) Range of growth temperatures

The tests using a temperature-gradient incubator showed that the strain grew in the range of 10° to 36° C. in Bennetti's broth.

(ii) Liquefaction of gelatin: positive
(iii) Hydrolysis of starch: positive
(iv) Coagulation of skim milk: negative
(v) Peptonization of skim milk: positive
(vi) Formation of melanoid pigment: positive

(d) Ability to assimilate carbon sources (on

Pridham and Gottlieb carbon utilization medium)
D-glucose, D-xylose, L-arabinose, L-rhamnose, D-fructose, D-galactose, D-mannitol, salicin, and sucrose are utilized for growth. No growth or only trace of growth with inositol and raffinose.

The above noted properties of the strain No. 9722 are summarized as follows: The aerial hyphae form spirals, the spore surface is smooth, the color of aerial the mycelium is brown-gray or grayish olive, and the strain gives positive melanoid pigment production and yields soluble red-purple pigment in certain media. For information on strains having such mycological properties, there were consulted Bergey's Manual of Determinative Bacteriology, the 7th edition (1957), ibid., the 8th edition (1974), Shirling and Gottlieb ISP (International Streptomyces Project) report (1968, 1969, and 1972), and "The actinomycetes" written by S. A. Waksman, Vol. 2 (1961). As a result, *Streptomyces violaceochromogenes* was found to be most close in nature to the strain No. 9722. That is, *S violaceochromogenes* is in good agreement with the strain No. 9722 in that the aerial mycelium is grey in color and forms spirals, the strain forms soluble red-purple pigment, the spore surface is smooth, and the strain is positive in the production of melanoid pigment (positive in a peptone-yeast-iron agar medium and negative in a tyrosin agar medium). Referring to the assimilation of sugars, *S. violaceochromogenes* is different from the strain No. 9722 in utilizing neither inositol nor raffinose.

The above slight difference in the utilization of sugars is not so significant that the strain No. 9722 and *S. violaceochromogenes* are considered to belong to different species. Accordingly, the strain No. 9722 was named *S. violaceochromogenes* No. 9722 and has been deposited as FERM BP-646 (Original Accession number FERM P-7362) in Fermentation Research Institute, Agency of Industrial Science and Technology, of 1-3, Higashi 1-chome, Yatabemachi, Tsukuba-gun, Ibaraki 305, Japan on Dec. 12, 1983, in conformity with Budapest Treaty on the International Recognition of the Deposit of Microorganisms for the Purposes of Patent Procedure.

For producing the s-AST-inactivating enzyme used in the present invention, the above strain is first cultivated in a nutrient medium to accumulate the enzyme. The cultivation can be carried out according to conventional methods for actinomycetes. For example, the nutrient medium contains carbon sources, nitrogen sources, and inorganic materials which the microorganism can utilize. Suitable carbon sources include, for example, glucose, fructose, maltose, sucrose, molasses, starch, dextrin, organic acids, and glycerol. Suitable nitrogen sources include organic nitrogen sources, for example, malt extract, peptone, yeast extract, dry yeast, meat extract, corn steep liquor, casein, and amino acids, and those inorganic nitrogen sources as for example, nitrates and ammonium salts. Suitable inorganic components include salts of potassium, sodium, magnesium, calcium, zinc, iron, and the like, which are used as required. An antifoaming agent such as a surfactant, silicone, or vegetable oil may be added to suppress the foaming during incubation.

The cultivation is preferred to be carried out under aerobic conditions with agitation by aeration or shaking. Any cultivation temperature may be chosen from the range where the strain grows and the s-AST-inactivating enzyme is produced, but the preferred temperature ranges within 20°–35° C. The desirable pH value of the culture medium ranges usually within 6–9. The cultivation period is chosen so as to give a maximum yield of the enzyme at the end of the period. It is usually in the range of 30 to 50 hours.

From a thus obtained culture, the s-AST-inactivating enzyme can be recovered by means of conventional protein purification techniques so as to utilize physical and chemical properties of the enzyme. For instance, after removal of the cells from the culture broth by filtration or centrifugation, the enzyme is purified by known techniques such as; salting out by use of ammonium sulfate, sodium sulfate, or the like; precipitation with an organic solvent such as ethanol, methanol, acetone, or the like; adsorption chromatography with, e.g. activated carbon, silica gel, alumina, hydroxyapatite, or cellulose; ion exchange chromatography with, e.g. ion exchange resin, ion exchange cellulose, or ion exchange Sephadex; gel filtration with, e.g. Sephadex or Bio-gel; and electrophoresis, ultrafiltration, and dialysis.

The s-AST-inactivating enzyme obtained in the above-mentioned process has the following physical and chemical properties:

(1) Action: The enzyme inactivates s-AST but not m-AST. It catalyzes the hydrolysis of proteins such as casein.

(2) Substrate specificity on protein: The enzyme is active on casein, hemoglobin, azocoll, and albumin.

(3) Optimum pH for the casein-hydrolyzing activity: The optimum pH was about 11.6 as estimated in solutions of substrate casein (1.33%) in Tris-HCl buffers (pH 7–9) and in glycine-NaOH buffers (pH 10–12).

(4) pH Stability: The enzyme was stable in the pH range of 5 to 6 after exposure to 37° C. for 14 hours.

(5) Optimum temperature for the casein-hydrolysing activity: For the hydrolysis of casein at pH 9.5 for 10 minutes, the maximum activity of the enzyme was obtained at 75° C.

(6) Thermal stability: Treatment at pH 8.5 for 10 minutes at different temperatures indicated that the enzyme retained 100% of the initial activity at 55° C. and 85% thereof at 65° C.

(7) Molecular weight: 17,500–18,000 (estimated by the SDS polyacrylamide gel electrophoretic method).

(8) Isoelectric point: 9.8 (calculated from electrofocussing method).

(9) Inhibitor: The enzyme activity was inhibited by phenylmethylsulfonyl fluoride but not by EDTA.

(10) Color and crystal form: White rhombohedral crystals.

A detailed description follows of the method for the fractional determination of AST isozymes by use of an s-AST-inactivating enzyme. According to the present invention, the s-AST in a liquid specimen is specifically inactivated by addition of the s-AST-inactivating enzyme. Then the residual AST activity, i.e. the m-AST in AST isozymes is separately determined by a known method of AST assay. The s-AST is determined by subtracting the obtained activity of m-AST from the total activity of AST isozymes which has been determined by the known method of AST assay.

The followings are known as typical prior art methods for AST determination (non-fractional).

A specimen is mixed and reacted with substrates (2-oxoglutaric acid and L-aspartic acid), the resulting oxaloacetic acid is reduced with malate dehydrogenase, and the simultaneous decrease in the quantity of reduced nicotinamide adenine dinucleotide (NADH) is measured (Karmen's method, J. Clin. Invest., 34, 126 (1955)).

The oxaloacetic acid formed as in the above method is reacted with dinitrophenylhydrazine, and the resulting coloring matter is determined by measuring the absorbance at 490–530 nm (Reitman-Frankel's method, Rinsho Kensa, 12, 398 (1968)).

The similarly formed oxaloacetic acid is reacted with a diazonium salt, and the resulting coloring matter is determined by measuring the absorbance at 500–550 nm (Clin. Chim. Acta. 7, 199 (1962) and Clin. Chem., 19, 776 (1973)). In the present invention, Karmen's method is particularly preferred.

A preferred embodiment of the method of the present invention is described below in more detail. A specimen, for example, serum is mixed with a buffer solution containing an s-AST-inactivating enzyme, serum albumin, and a coenzyme pyridoxal phosphate. The mixture is pre-incubated at 10°–40° C. for 1–30 minutes to inactivate the s-AST. A buffer solution containing aspartic acid, 2-oxoglutaric acid, malate dehydrogenase, and NADH is added to the mixture and the reaction is carried out at 25°–37° C. Then the decrease in the NADH concentration is determined by measuring the absorbance at 340 nm. The m-AST activity is determined by comparing this absorbance value with a calibration curve which has been obtained by the above procedure using standard specimens of known m-AST concentrations. The s-AST activity is determined by subtracting the obtained activity of m-AST from the total activity of AST isozymes which has been determined by the same procedure as the above except for adding no s-AST-inactivating enzyme.

The cytosolic aspartate aminotransferase isozyme inhibiting composition according to the present invention contains an effective amount of an s-AST-inactivating enzyme to inhibit s-AST. The composition according to the present invention contains additionally a composition for assaying AST activity to fractionally determining AST isozymes. The compositions for assaying AST activity include typically the compositions for use in the Karmen method, Reitman-Frankel method, and the like. For example, the composition according to the present invention most typically comprises an s-AST-inactivating enzyme, pyridoxal phosphate, serum albumin, aspartic acid, 2-oxoglutaric acid, NADH, malate dehydrogenase, and a buffer.

The amount of an s-AST-inactivating enzyme to be employed in the method or composition according to the present invention is dependent on the temperature and time of the incubation. Generally, the amount per one Karmen unit of s-AST is 0.005–5.0 units in terms of the following AST inhibitory activity.

The s- and m-AST inhibitory activity of the enzyme according to the present invention is assayed in the following manner: 0.5 ml of the s-AST-inactivating enzyme solution is mixed with 0.5 ml of 50 mM Tris-HCl buffer (pH 8.5) containing s-AST or m-AST (50 Karmen units, each prepared from pig heart according to the method of Y. Morino et al., J. Biochem., 82, 847–852 (1977)), bovine serum albumin (0.1 mg/ml) and pyridoxal phosphate (4 $\mu$M). The reaction mixture is incubated at 25° C. for 15 minutes, and then mixed with 3.0 ml of 50 mM Tris-HCl buffer (pH 8.0) containing aspartic acid (20 mM), 2-oxoglutaric acid (10 mM), NADH (0.2 mM), and malate dehydrogenase (10 units, supplied by Oriental Yeast Co., Ltd.) to initiate the reaction at 25° C. The decrease per minute in the absorbance at 340 nm is measured. Comparing the absorption value thus found with the value obtained by the above procedure but using water instead of the inactivating enzyme, the inhibitory activity of the enzyme which reduces the absorbance to 50% of the latter value is defined as one unit.

The present invention is illustrated in more detail with reference to the following examples.

TEST EXAMPLE 1

Production of s-AST-inactivating enzyme by *Streptomyces violaceochromogenes* No. 9722

A loop of *Streptomyces violaceochromogenes* No. 9722 (FERM BP-646) from an agar slant culture was inoculated to 100 ml of a medium (pH 7.0) comprising 1.0% glucose, 1.0% polypeptone, 1.0% meat extract, 0.3% sodium chloride, and 0.02% Adekanol (tradename of an anti-foaming agent supplied by Asahi Denka Co., Ltd.) in a 500-ml shaking flask. The culture was grown for 40 hours at 30° C. with reciprocal shaking to prepare a seed culture broth. A medium (18 l) of the same composition as in the above was charged in a 30-l jar fermenter, and the above seed culture was inoculated and grown at 28° C. under an inner pressure of 0.5 Kg/cm$^2$ for 40 hours with aeration (9 l/min) and agitation (300 rpm).

The resulting culture broth was filtered to remove the cells, and the filtrate was 80% saturated with ammonium sulfate, left standing overnight. The resulting precipitate was collected by centrifugation, and dissolved in a 50 mM acetate buffer (pH 4.0). The solution was dialyzed against a buffer of the same composition by means of a cellophane tube. The dialyzed solution was charged on an SP-Sephadex C-50 (supplied by Pharmacia Fine Chemical Co.) column (4.8 cm$\phi$×28 cmL), which had been pre-equilibrated with a buffer of the same composition before use, then eluted with 0-0.6 M NaCl gradient. The active fractions eluted with 0.25 to 0.3 M NaCl solution were collected and 80% saturated with ammonium sulfate. The resulting precipitate was collected by centrifugation, and dissolved in a 40 mM boric acid-KOH buffer (pH 9.7). This enzyme solution was dialyzed against a buffer of the same composition, and passed through a DEAE-Sephadex A-25 (supplied by Pharmacia Fine Chemical Co.) column (2.0cm$\phi$×10 cmL) which had been pre-equilibrated with a buffer of the same composition before use. The enzyme, weakly adsorbed on this resin, was eluted by successive passage of the same buffer. Ammonium sulfate was dissolved in the eluate to 80% saturation, and the resulted precipitate was collected by centrifugation. The precipatate was dissolved in a 40 mM boric acid-KOH buffer (pH 9.7). This enzyme solution was dialyzed against a buffer of the same composition, the precipitate formed during dialysis was removed by filtration, the resulting solution of the enzyme was left standing at a low temperature, and thus the s-AST-inactivating enzyme was obtained in crystalline form.

TEST EXAMPLE 2

Comparison of AST isozyme inhibitory activity of the enzyme produced by *Streptomyces violaceochromogenes* No. 9722 with that of various known proteases.

AST isozyme inhibitory activities of the following proteases were assayed according to the method described above. Results thereof expressed in residual activities of s-AST and m-AST are shown in Table 2. The amount of each protease used in the assay was determined by measuring the casein-hydrolyzing activity thereof; that is, the substrate casein and each protease were reacted at 37° C. for 10 minutes, Folin's reagent was added to the trichloroacetic acid-soluble fraction, and the resulting blue color, i.e. the absorbance at 660 nm, was measured. Thus the amount of each protease was expressed in the found optical density (OD) value. Proteases assayed:

(1) s-AST-inactivating enzyme produced by *Streptomyces violaceochromogenes* No. 9722;

(2) Pronase (tradename of an enzyme supplied by Kaken Kagaku Co., Ltd.); before use, it was freed from the metal protease activity by the affinity chromatography with a metal protease inhibitor;

(3) Subtilisin BPN' (supplied by Nagase Sangyo Co., Ltd. under the tradename of Nagase);

(4) Subtilisin Carlsberg (Meth. Enzymol., 19; 179-215 (1970));

(5) Alkaline protease produced by a strain of genus Cepharosporium (J. Yagi et al., J. Ferment. Technol., 50, 592-599 (1972));

(6) Protease produced by *Aspergillus melleus* (Ito et al., Yakugaku Zassi, 88, 1576-1582 (1968)); (7) Alkaline protease produced by *Aspergillus oryzae* (Hayashi, Kagaku to Seibutsu, 11, 82-89 (1973)); (8) Alkaline protease produced by *Penicillium lilacinum* (M. Arai et al., Agric. Biol. Chem. 41, 2293-2294 (1977)); (9) Alkaline protease produced by *Candida lipolytica* (S. Tobe et al., Argic. Biol. Chem., 40, 1087-1092 (1976)); 10 Thermolysin, a neutral protease produced by *Bacillus thermoproteolyticus* (H. Matsubara et al., The Enzymes, 3rd Edition, p.721, published by Academic Press. in 1970);

(11) Trypsin;
(12) α-Chymotrypsin;
(13) Papain;
(14) Ficin; and
(15) Bromelain.

TABLE 2

| Name of enzyme or microorganism producing the enzyme | Amount of protease used (OD) | Residual activity of s-AST (%) | Residual activity of m-AST.(%) |
|---|---|---|---|
| S. violaceochromogenes No. 9722 | 0.13 | 0 | 98 |
| Pronase | 1.2 | 38 | 100 |
| Subtilisin BPN' | 0.63 | 8 | 97 |
| Subtilisin Carlsberg | 0.75 | 14 | 100 |
| Cepharosporium | 0.93 | 38 | 86 |
| A. melleus | 0.96 | 68 | 99 |
| A. oryzae | 0.85 | 65 | 94 |
| P. lilacinum | 0.73 | 100 | 100 |
| C. lipolytica | 0.31 | 94 | 97 |
| Thermolysin | 0.83 | 100 | 100 |
| Trypsin | 0.46 | 86 | 100 |
| α-Chymotrypsin | 0.90 | 78 | 100 |
| Papain | 0.80 | 97 | 100 |
| Ficin | 0.78 | 100 | 99 |
| Bromelain | 0.94 | 97 | 99 |

From Table 2, s-AST proves to be inactivated by enzymes belonging to serine protease group which are produced by microorganisms, that is, enzymes such as the s-AST-inactivating enzyme produced by *Streptomyces violaceochromogenes* No. 9722, Pronase, and Subtilisin, but not inactivated by a metal protease (Thermolysin) or a thiol protease (Papain, Ficin or Bromelain). Although belonging to the serine protease group, the protease produced by *Penicillium lilacium* or by *Candida lipolytica* shows no s-AST inhibitory activity and trypsin and αochymotrypsin, which are produced by animals, show weak s-AST inhibitory activity. All the proteases presented in Table 2 show no or slight m-AST inhibitory activity. The enzyme produced by *Streptomy-* ces violaceochromogenes No. 9722, found by the present inventors, is advantageous over known serine proteases in higher s-AST specificity and in higher s-AST inhibitory activity per casein-hydrolyzing activity. That is, larger amounts of the above known serine proteases than that used in this test example were required to inhibit s-AST completely.

TEST EXAMPLE 3

Figure 2:
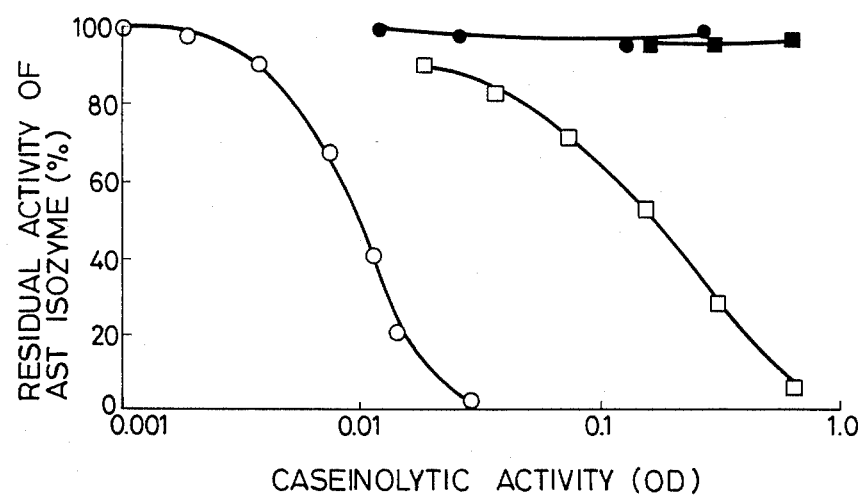
FIG. 2 shows the relationship between caseinolytic activities of the above enzymes and AST inhibitory activites thereof.

Relationship between dose of s-AST-inactivating enzyme and AST inhibitory activity thereof:

AST inhibitory activities of the enzyme produced by Streptomyces violaceochromogenes No. 9722 was compared with those of subtilisin BPN'. That is, according to the above described method for the determination of inhibitory activity, residual activities of AST isozymes were assayed varying the amounts (weights) and casein-hydrolyzing activities of the enzyme used. As shown in FIGS. 1 and 2, the enzyme produced by Streptomyces violaceochromogenes No. 9722 inactivated s-AST completely with less than 1/5 of subtilisin BPN' by weight or about 1/20 by the casein-hydrolyzing activity thereof. No inactivation of m-AST by the former enzyme was observed under the same condition.

EXAMPLE 1

Using 20 samples of serum, m-AST isozyme therein was assayed. Each sample (200 µl) was mixed with 1.0 ml of a 50 mM Tris-HCl buffer (pH 8.5) containing the s-AST-inactivating enzyme (200 unit/ml, produced by Streptomyces violaceochromogenes No. 9722), bovin serum albumin (0.1 mg/ml), and pyridoxal phosphate (4 µM). To the mixture incubated at 37° C. for 15 minutes, was added 3.0 ml of a 50 mM Tris-HCl buffer (pH 8.0) containing aspartic acid (20 mM), 2-oxoglutaric acid (10 mM), NADH (0.2 mM), and malate dehydrogenase (10 units, supplied by Oriental Yeast Co., Ltd.) to initiate the reaction at 37° C. The decrease per minute in the absorbance at 340 nm was measured. The activity of the m-AST was determined by comparing this absorbance value with a calibration curve which had been obtained by the above procedure using standard specimens of known m-AST concentrations.

For comparison, m-AST in the same serum spcimens was assayed by using "Eiken" (supplied by Eiken Kagaku Co., Ltd., and see Japanese Patent Laid-Open No. 02553/81 and Chem. Abst. 94 98836 r), which is a reagent for m-AST assay according to a known immunochemical method.

Results of the assay are shown in Table 3. Good correlation (correlation coefficient 0.976) was observed between the found values according to the method of the present invention and to the known method.

TABLE 3

| Specimen No. | Activity of m-AST (Karmen units) | |
|---|---|---|
| | Method of the present invention | Known method |
| 1 | 4 | 3 |
| 2 | 6 | 8 |
| 3 | 9 | 12 |
| 4 | 12 | 9 |
| 5 | 6 | 8 |
| 6 | 13 | 14 |
| 7 | 5 | 7 |
| 8 | 17 | 21 |
| 9 | 10 | 8 |
| 10 | 7 | 5 |
| 11 | 24 | 29 |
| 12 | 19 | 15 |

TABLE 3-continued

| Specimen No. | Activity of m-AST (Karmen units) | |
|---|---|---|
| | Method of the present invention | Known method |
| 13 | 35 | 31 |
| 14 | 18 | 21 |
| 15 | 23 | 27 |
| 16 | 30 | 24 |
| 17 | 44 | 40 |
| 18 | 36 | 41 |
| 19 | 73 | 66 |
| 20 | 50 | 56 |

EXAMPLE 2

The procedure of Example 1 was repeated except for using subtilisin BPN' in place of the s-AST-inactivating enzyme. The correlation coefficient between the found values according to the two methods was 0.968.

EXAMPLE 3

The procedure of Example 1 was repeated except for using Pronase in place of the s-AST-inactivating enzyme. The correlation coefficient between the found values according to the two methods was 0.963.

EXAMPLE 4

Using serum as a specimen, m-AST therein was assayed in the same manner as used in Example 1. Then the total AST was assayed by the same procedure but without using the s-AST-inactivating enzyme for the reaction. The found activity of m-AST was 17 Karmen units and that of total AST was 123 Karmen units. From the difference between these values, the activity of s-AST was determined as 106 Karmen units.

What is claimed is:

1. A method of inactivating cytosolic aspartate aminotransferase isozyme comprising addition of an effective cytosolic aspartate aminotransferase isozyme inhibitory amount of a specific inhibitory enzyme, wherein said specifc inhibitor enzyme is not trypsin.

2. A method of claim 1 wherein said inhibitory enzyme is a serine protease produced by microorganism.

3. A method of claim 2 wherein the serine protease is an enzyme produced by Streptomyces violaceochromogenes No. 9722 (FERM BP-646).

4. A method for the fractional determination of aspartate aminotransferase isozyme activities, which comprises (a) determination of the total isozyme activity of the specimen, (b) inactivating the cytosolic aspartate aminotransferase isozyme in a reaction mixture containing the specimen by the addition of an effective cytosolic aspartate aminotransferase isozyme inhibitory amount of a specific inhibitory enzyme, followed by determination of the residual mitochondrial aspartate aminotransferase isozyme activity, and (c) determination of the cytosolic isozyme activity by subtracting the activity of mitochondrial isozyme determined in (b) from the total activity of aspartate aminotransferase isozymes determined in (a).

5. A method of claim 4 wherein said inhibitory enzyme is a serine protease produced by microorganism.

6. A method of claim 5 wherein the serine protease is an enzyme produced by Streptomyces violaceochromogenes No. 9722 (FERM BP-646).

7. A method of claim 4 wherein the specimen is body fluid.

8. A method of claim 7 wherein the body fluid is blood serum.

9. A cytosolic aspartate aminotransferase isozyme inhibiting composition containing an effective cytosolic aspartate aminotransferase isozyme inhibitory amount of a specific inhibitory enzyme, wherein said specific inhibitory enzyme is produced by *Streptomyces violaceochromogenes*.

10. A composition according to claim 9 wherein the specific inhibitory enzyme is a serine protease.

11. A composition according to claim 9 wherein the *Streptomyces violaceochromogenes* is *Streptomyces violaceochromogenes* No. 9722 (FERM BP-646).

12. A composition according to claim 9 wherein said composition contains an aspartate aminotransferase activity assay composition.

* * * * *